(12) United States Patent
Redmond et al.

(10) Patent No.: US 6,641,571 B2
(45) Date of Patent: Nov. 4, 2003

(54) REDUCTION OF POSTOPERATIVE COMPLICATIONS OF CARDIOPULMONARY BYPASS (CPB) SURGERY

(75) Inventors: H. Paul Redmond, Wilton (IE); Rolf W. Pfirrmann, Lucerne (CH)

(73) Assignee: Ed. Geistlich Soehne AG fuer Chemische Industrie (CH)

(*) Notice: Subject to any disclaimer, the term of this patent is extended or adjusted under 35 U.S.C. 154(b) by 156 days.

(21) Appl. No.: 09/753,719

(22) Filed: Jan. 4, 2001

(65) Prior Publication Data

US 2002/0035996 A1 Mar. 28, 2002

Related U.S. Application Data

(60) Provisional application No. 60/174,606, filed on Jan. 5, 2000, and provisional application No. 60/245,325, filed on Nov. 3, 2000.

(51) Int. Cl.[7] ............................................. A61M 31/00
(52) U.S. Cl. ..................................... 604/508; 128/898
(58) Field of Search ............................. 604/500, 507, 604/508, 509; 128/898

(56) References Cited

U.S. PATENT DOCUMENTS

| | | | |
|---|---|---|---|
| 4,337,251 A | | 6/1982 | Pfirrmann |
| 4,548,597 A | * | 10/1985 | Nelson ........................ 604/43 |
| 4,626,536 A | | 12/1986 | Pfirrmann |
| 4,889,137 A | * | 12/1989 | Kolobow .................... 128/898 |
| 5,077,281 A | | 12/1991 | Reinmueller |
| 5,210,083 A | | 5/1993 | Pfirrmann |
| 5,417,975 A | | 5/1995 | Lussi et al. |
| 5,763,421 A | | 6/1998 | Caretto et al. |
| 6,011,030 A | * | 1/2000 | Pfirrmann ................ 514/222.2 |
| 6,258,797 B1 | * | 7/2001 | Lehner .................... 514/222.5 |

FOREIGN PATENT DOCUMENTS

| | | |
|---|---|---|
| DE | 196 06 897 A1 | 8/1997 |
| EP | 1 040 841 A1 | 10/2000 |
| JP | 61000017 | 1/1986 |
| WO | WO 88/05301 A1 | 7/1988 |
| WO | WO 92/00743 A1 | 1/1992 |
| WO | WO 95/18638 A1 | 7/1995 |
| WO | WO 95/30423 A2 | 11/1995 |
| WO | WO 98/28027 A1 | 7/1998 |
| WO | WO 99/06114 A2 | 2/1999 |
| WO | WO 00/01391 A1 | 1/2000 |

OTHER PUBLICATIONS

Bennett–Guerrero, E., et al., "Relationship of Preoperative Antiendotoxin Core Antibodies and Adverse Outcomes Following Cardiac Surgery", *JAMA*, Feb. 26, 1997, vol. 277, No. 8, pp. 646–650.

Kuan, P., et al., "Coronary Artery Bypass Surgery Morbidity", *JACC*, Jun. 1984, vol. 3, No. 6, pp. 1391–1397.

Tonnesen, E., et al., "The Role of Cytokines in Cardiac Surgery", *International Journal of Cardiology*, 53 Suppl., pp. S1–S10 (1996).

C.A. Jacobi et al., Peritoneale instillation von Taurolidin und Heparin zur Verhinderung von intraperitonealem Tumorwaschstum und Trokarmetastasen bei laparoskopischen Operationen im Rattenmodell, Langenbecks Arch Chir, Jul. 25, 1997, pp. S31–S36, vol. 382, No. 4, suppl. 1.

K.H. Treutner et al., Prevention of postoperative adhesions by single intraperitoneal medication, Journal of Surgical Research (1995) vol. 59. No. 6, pp. 764–771. (Abstract only).

R. Brat et al., Comparison between blood and crystalloid cardioplegia in patients with left ventricular dysfunction undergoing coronary surgery, Acta Medica (Hradec Karalove) (2000), vol. 43, No. 3, pp. 107–110. (Abstract only).

* cited by examiner

*Primary Examiner*—Edward K. Look
*Assistant Examiner*—John K Fristone, Jr.
(74) *Attorney, Agent, or Firm*—Rothwell, Figg, Ernst & Manbeck

(57) ABSTRACT

Patients undergoing cardiopulmonary bypass surgery are treated perioperatively with methylol transfer agents, such as Taurolidine. Patients undergoing crystalloid cardioplegia who are treated with taurolidine show reduced levels of IL-6 and increased levels of IL-10 when compared to crystalloid cardioplegia patients administered a placebo. Crystalloid cardioplegia patients administered Taurolidine also show reduced levels of IL-6 and increased levels of IL-10 when compared to blood cardioplegia patients who were administered Taurolidine.

29 Claims, No Drawings

REDUCTION OF POSTOPERATIVE COMPLICATIONS OF CARDIOPULMONARY BYPASS (CPB) SURGERY

BACKGROUND OF THE INVENTION

The physiological and immunological alterations induced in patients undergoing interventive cardiac surgery necessitating cardiopulmonary bypass (CPB) have been well established in recent years. The sequential elevation of systemic cytokine levels have also been shown to result in the depletion of cardiac myocyte amino acids such as taurine and in an in vitro model the reduction in ICAM-1 expression on endothelial cells. Studies showed that post reperfusion taurine levels were low in both blood and crystalloid cardioplegia patients.

The most important of the initiating stimuli responsible for the release of such proinflammatory mediators is debated; however, the development of a systemic endotoxemia is considered to be a significant prognostic factor. It is well established that endotoxin (or lipopolysaccharide), itself a bacterial cell wall product, has been recognized as a potent proinflammatory cell activator both in vivo and in vitro. A systemic endotoxemia has been clearly demonstrated to occur in patients undergoing CPB. This occurs following the release of the aortic cross clamp. The pathophysiological mechanism underlying this endotoxemia has been suggested as being secondary to bacterial translocation following inadvertent gut ischemia. The efficacy of the host response to this endotoxemia has direct implications for the development of postoperative morbidity. A low preoperative titer of IgM anti-endotoxin core antibody has been used as an independent prognostic indicator of host outcome following CPB in one study, thus emphasizing the significance of endotoxin. Another group suggested that the interleukin-6 (IL-6) systemic elevation, which also occurs in CPB patients, is a direct consequence of this early systemic endotoxemia and may in turn be responsible for the post-reperfusion sequelae. One group in particular suggested that the major cause of reperfusion injury is through the iron mediated generation of the hydroxyl radical (OH). They demonstrated that the use of highly diffusible desferri-exochelins block injury caused by OH production and have potential for the treatment of reperfusion injury.

Taurolidine (bis(1,1-dioxoperhydro-1,2,4-thiadiazin-4-yl) methane) has been employed as a clinically effective therapeutic agent for many years. The compounds taurolidine and taurultam are as disclosed in U.S. Pat. No. 5,210,083, incorporated herein by reference. Taurolidine has been utilized both for antibacterial prophylaxis and as a therapeutic bactericidal agent in peritoneal sepsis. It has a short half life and is rapidly metabolized to taurine, carbon dioxide and water. Taurolidine has been shown to have a broad spectrum of antimicrobial activity against both gram positive and gram negative bacteria and fungi and has a neutralizing activity against bacterial endotoxin. There is no definite treatment available for reperfusion injury. Taurine, one of the key metabolites of taurolidine, has been shown to possess significant therapeutic properties of its own including endothelial cell membrane stabilization, proinflammatory cell antiapoptotic and antioxidant capability and homeostatic cellular osmoregulation. In some animal studies results indicated that taurine protects ischemic heart muscle against reperfusion induced arrhythmias, through its properties both as a membrane stabilizer and an oxygen free radical scavenger. Taurolidine has been shown to be non-toxic to humans and animals and is free from side effects following intravenous and intraperitoneal administration. This wide spectrum of antiseptic properties has led to its clinical application in conditions ranging from osteomyelitis to peritonitis and catheter related sepsis prophylaxis.

SUMMARY OF THE INVENTION

In accordance with the present invention, a method of reducing postoperative complications of cardiopulmonary bypass (CPB) surgery in a patient comprises administering to the patient an effective amount of a methylol transfer agent in conjunction with CPB surgery of said patient.

DETAILED DESCRIPTION OF THE INVENTION

To prevent postoperative complications, in particular damage of the myocardium by reperfusion, e.g., arrhythmia, intravenous administration of taurolidine or taurultam solutions is performed intraoperatively.

Disturbances of the rhythmic center and conduction system of the heart due to formation of myocardium-damaging peroxides during reperfusion may lead to sinus-arrhythmia, ventricular-fibrillation and fluttering. Such complications can be avoided by intraoperative intravenous administration of taurolidine or taurultam solutions.

An additional effect is the protection from much feared infections and toxemia such as streptococci, enterococci, klebsiella, pseudomonas and serratia, inclusive of mycotic infections as candida or aspergillus, for prevention of acute myocarditis, pericarditis and endocarditis.

Intraoperative dosages may be in the range of about 10–20 grams taurolidine or taurultam as active ingredient, or combination of both substances in about a 2% hypotonic solution or in about a 1% isotonic Ringer's solution as drop infusion via a central vein catheter.

The present invention is applicable to any suitable methylol transfer agent that reduces postoperative complications of CPB surgery in a patient. Although the invention is further described with respect to the methylol transfer agents Taurolidine and/or Taurultam, it is to be understood that the invention is equally applicable to any suitable methylol transfer agent having activity similar to or substantially the same as Taurolidine and/or Taurultam.

Methylol transfer agents in accordance with the present invention can be administered in any suitable form, such as orally administered tablets or capsules, or intravenously administered solutions.

In preferred embodiments, 250 ml of Taurolidine 2% solution is administered by intravenous infusion about 1–6 times per day, more preferably about 2–4 times per day during the treatment period.

One or more methylol transfer agents in accordance with the present invention can be administered before, during and/or after CPB surgery.

In accordance with preferred embodiments, 2% Taurolidine solution is administered by intravenous infusion to a CPB patient during surgery, and the patient receives about 250 ml doses per day at about 12 hour intervals following the CPB surgery.

In accordance with one embodiment, perioperative administration of the anti-endotoxins taurolidine and/or taurultam is utilized in the attenuation of the post-reperfusion sequelae in patients subjected to cardiopulmonary bypass. It is believed that the invention may affect:

(i) reduction of septic complications following CPB;

(ii) reduction of reperfusion induced arrhythmias in blood cardioplegia and crystalloid cardioplegia patients;

(iii) amelioration of systemic endotoxemia and proinflammatory cytokine activation in the perioperative period; and (iv) reduction in respiratory compromise seen in post CPB patients.

In preferred embodiments, the present invention utilizes an established non-toxic antiseptic, antiendotoxin and antioxidant agent such as taurolidine and/or taurultam in the amelioration of the post operative physiological morbidity associated with CPB surgery. In preferred embodiments, the present invention utilizes perioperative taurolidine in the clinical setting of cardiac surgery to impact post-operative reperfusion induced arrhythmias, sepsis, inotropic support and in turn early mobilization and reduction in the hospital stay and improvement of clinical prognostic indicators in patients undergoing CPB with both crystalloid and blood cardioplegia techniques.

It is believed that through the therapeutic amelioration of the early systemic endotoxemia seen in CPB patients, attenuation of the proinflammatory mediator cascade may be achieved. This is believed to result in a reduction in the postoperative cytokine mediated sequelae, and ultimately result in an improved clinical outcome of CPB patients.

Aortic unclamping during cardiopulmonary bypass is the ultimate ischemia reperfusion injury and is characterized by marked derangement of the systemic inflammatory response (SIRS). Taurolidine, a potent anti-inflammatory antioxidant, has proven efficacy in patients with SIRS following pancreatitis. This invention shows the benefits of taurolidine treatment in patients subjected to CPB.

The present invention is described by reference to the following Examples, which are offered by way of illustration and are not intended to limit the invention in any manner. Standard techniques well known in the art or the techniques specifically described below were utilized.

EXAMPLE 1

| 1% Taurolidine, 1% Taurultam Solution | |
|---|---|
| 1000 mL 2% Solution of Taurolidine/Taurultam: | |
| Taurolidine | 10 g |
| Taurultam | 10 g |
| Hydroxyethyl starch (substitution grade 0.4–0.5) | 50 g |
| Water for injection | to 1000 mL |

The solution is prepared with heating at approximately 60° C. with stirring in a closed stainless steel container. After cooling to room temperature, the pH is adjusted to 7.6. The solution is passed through a 0.2 and 0.1 μm sterile filter and placed in 250 mL bottles which are sterilized at 121° C. for 15 minutes.

EXAMPLE 2

2% Taurolidine Solution

The solution is prepared as in Example 1 except that 20 grams of taurolidine are added and no taurultam is added.

EXAMPLE 3

| 1% Taurolidine Ringer Solution | |
|---|---|
| 1000 mL 1% Taurolidine Ringer Solution | |
| Taurolidine | 10 g |
| Sodium chloride | 6 g |
| Potassium chloride | 0.075 g |
| Calcium chloride 6 H$_2$O | 0.15 g |
| Sodium hydrogen carbonate | 0.075 g |

| 1% Taurolidine Ringer Solution | |
|---|---|
| Povidone UP (M.W. 10,000) | 12.5 g (see U.S. Pat. No. 6,080,397) |
| Water for injection | to 1000 mL |

The solution is prepared as in Example 1.

EXAMPLE 4

| 2% Taurolidine Solution | |
|---|---|
| 1000 mL 2% Taurolidine Solution | |
| Taurolidine | 20 g |
| Povidone UP (M.W. 10,000) | 50 g (see U.S. Pat. No. 6,080,397) |
| Water for injection | to 1000 mL |

The solution is prepared with heating at approximately 60° C. with stirring in a closed stainless steel container. After cooling to room temperature, the pH is adjusted to 7.6. The solution is passed through a 0.1 and 0.1 μm sterile filter and placed into infusion bottles of 100 or 250 mL. The bottles are closed and sealed and sterilized at 121° C. for 15 minutes.

EXAMPLE 5

| 1% Taurolidine/1% Taurultam in Isotonic Sodium Chloride Solution | |
|---|---|
| 1000 mL 1% Taurolidine/1% Taurultam in Isotonic Sodium Chloride Solution | |
| Taurolidine | 10 g |
| Taurultam | 10 g |
| Hydroxyethyl starch (substitution grade 0.4–0.5) | 60 g |
| Sodium chloride | 9 g |
| Glucose monohydrate for injection | 20 g |
| Water for injection | to 1000 mL |

The solution is prepared by dissolving the components without glucose in distilled water with heating at approximately 50° C. After cooling to room temperature, the pH is adjusted to 7.2. The solution is filtered at room temperature through a 0.2 μm sterile filter into a second container with stirring into which the glucose was previously placed. The mixture is stirred briefly and filtered through a 0.1 μm sterile filter. The solution is placed into sterile glass bottles under a laminar flow hood and the bottles are closed and sealed.

EXAMPLE 6

A randomized prospective clinical trial was performed. Thirty-four consecutive patients with an ejection fraction >30%, undergoing elective coronary artery bypass grafting were randomized into four groups. Groups A and B received taurolidine (250 mL 2% taurolidine) intravenously at induction through a central line. These patients also received two further doses of taurolidine at 12 hour intervals (2×250 mL 2% taurolidine/day) for the first 24 hours following surgery, but in group A crystalloid cardioplegia was used for myocardial protection and in group B blood cardioplegia was used. Groups C and D received saline vehicle controls while group C had crystalloid cardioplegia and group D received blood cardioplegia. Blood samples were taken preoperatively, at the time of aortic unclamping, 2 hours, 6 hours and 24 hours post aortic unclamping. Neutrophil and monocyte respiratory burst, phagocytosis ability, CD11b and CD14 expression were assessed using flow cytometry. Plasma interleukins 6, 8 and 10 (IL-6, IL-8 and IL-10) and tumor necrosis factor α (TNF-α) were determined by Enzyme Linked Immuno Sorbent Assay. All the patients received the standard antibiotic prophylaxis for cardiac bypass surgery.

Patient selection was performed as follows. Patients undergoing elective coronary artery bypass grafting with an ejection fraction greater than or equal to 30%, no history of Diabetes mellitus and a normal chest x-ray were selected. Patients on ACE-inhibitors were not included in the study. The decision was made jointly by the consultant anesthetist and surgeon involved before inclusion in the study, and each patient was then randomized to drug or control. All the patients were nursed in the cardiac intensive care unit post operatively. Informed consent was sought from each patient before inclusion into the study.

Assessment of the patients included the following:
Preoperatively:

| 1. | Clinical assessment | Left ventricular function ECG, chest x-ray. |
|---|---|---|
| 2. | Whole Blood | Serum VEGF, Serum GM CSF, Serum Cytokines (IL-6, IL-8, IL-10, TNF-α) Blood cultures (aerobic and anaerobic). |
| 3. | Neutrophil/Monocyte activation state. (CD11b, CD14, Respiratory Burst, Phagocytosis ability) | |
| 4. | Lipopolysaccharide binding protein (LBP). | |
| 5. | Serum Endotoxin (pre-op, on bypass, cross clamp off, 1 hour post clamp off, 2 hours post clamp off, 4 hours and 24 hours post operatively). | |

Parameters 2–4 were assessed post aortic unclamping, 2 hours and 24 hours post-operatively.
Post-Operatively:
 1. Continuous E.C.G. monitoring for first 72 hours.
 2. 12 lead E.C.G.s on Days 1, 2, 3 and 4 and prior to discharge.
 3. Pulse (rate/rhythm).
 4. Temperature.
 5. W.B.C. Count on Days 1, 2, 5 and 8.
 6. Chest X-ray on Days 1, 2, 5 and 8.
 7. Inotropic support (type, quantity and duration).

Thirty-four patients were studied as described above. The patients were divided as follows:

| Total Number of Patients: 34 | |
|---|---|
| Group A: crystalloid cardioplegia and taurolidine | 8 patients |
| Group B: blood cardioplegia and taurolidine | 9 patients |
| Group C: crystalloid cardioplegia and placebo | 8 patients |
| Group D: blood cardioplegia and placebo | 9 patients |

The tests performed on the patients were as follow:
Laboratory Results Analyzed
 1) Neutrophil and Monocyte Activity
   a) Respiratory burst
   b) Phagocytosis
   c) CD11b
   d) CD14
 2) Cytokines
   a) Interleukin-6
   b) Interleukin-10
   c) TNF-α
   d) Interleukin-8
Laboratory results include:
 1) Interleukin-1β
 2) VGEF
 3) Endotoxin (LPS)
The results of the tests are presented below.

TABLE 1

Serum IL-6 and IL-10 Levels at 24 Hours Post Aortic Unclamping

| | IL-6 (pg/mL) | IL-10 (pg/mL) |
|---|---|---|
| Placebo (n = 8) (Group C) | 21.3 ± 3.5 | 7.9 ± 3.9 |
| Taurolidine (n = 8) (Group A) | 8.0 ± 1.4* | 28.2 ± 9.6* |

Data = mean ± s.d.; Statistics by Student's t-test; *$p < 0.05$ vs. Placebo

The results of Table 1 indicate that interleukin-6 was significantly down-regulated in patients who were administered taurolidine (Group A) perioperatively as compared to placebo group (Group C) at the 24 hour timepoint in the crystalloid cardioplegia groups. No beneficial effect was seen in combination with blood cardioplegia (Group B vs. Group D). Interleukin-10 was significantly up-regulated in patients who were administered taurolidine (Group A) perioperatively as compared to the placebo group (Group C) at the 24 hour timepoint in the crystalloid cardioplegia groups. Administration of taurolidine in patients undergoing CPB significantly reduced circulating IL-6 and increased IL-10 production when compared to placebo ($p<0.05$ at 24 hours post aortic unclamping).

These results demonstrate that perioperative administration of taurolidine attenuates reperfusion injury in patients undergoing coronary artery bypass surgery by modulating pro-and anti-inflammatory cytokine production.

Additional data demonstrated that Interleukin-6 was significantly down-regulated in crystalloid cardioplegia group (Group A) as compared to the blood cardioplegia group (Group B) in the taurolidine administered patients. Interleukin-10 was significantly up-regulated in the crystalloid cardioplegia group (Group A) as compared to the blood cardioplegia group (Group B) in the taurolidine administered patients. Administration of taurolidine in crystalloid cardioplegia patients resulted in reduced circulating IL-6 and increased IL-10 production when compared to blood cardioplegia ($p<0.05$ at 24 hours post aortic unclamping). Taurolidine treatment did not appear to modify neutrophil or monocyte activity or circulating TNF-α or IL-8.

EXAMPLE 7

Effect of Taurolidine on Arrhythmia during Crystalloid Cardioplegia

Ten patients underwent CPB using crystalloid cardioplegia with taurolidine 2% solution for myocardial protection. Another ten patients underwent CPB using crystalloid cardioplegia and a placebo for myocardial protection. Three of the patients treated with taurolidine experienced arrhythmia whereas 8 of the patients treated with placebo experienced arrhythmia.

The results demonstrate that taurolidine may have a protective role in CPB patients subjected to crystalloid cardioplegia by up-regulating the anti-inflammatory cytokine IL-10 and down-regulating the pro-inflammatory cytokine IL-6. Based on the above results, it further appears that taurolidine may reduce arrhythmia in CPB patients.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method of reducing postoperative complications including myocardium damage by reperfusion associated with cardiopulmonary bypass (CPB) surgery in a patient, comprising administering to a patient an effective amount of a methylol transfer agent in conjunction with CPB surgery of said patient.

2. The method of claim 1 wherein said agent is selected from the group consisting of taurolidine, taurultam and mixtures thereof.

3. The method of claim 2 wherein said agent is administered to said patient during a time period selected from the group consisting of prior to said CPB surgery, during said CPB surgery, subsequent to said CPB surgery and combinations thereof.

4. The method of claim 2 wherein said agent comprises taurolidine solution.

5. The method of claim 4 wherein said solution is a 2% taurolidine solution.

6. The method of claim 5 wherein said taurolidine solution is administered to said patient at a dose of 250 mL.

7. The method of claim 6 wherein said patient receives two said doses per day at about 12 hour intervals following said surgery.

8. A method of reducing postoperative complications of cardiopulmonary bypass (CPB) surgery in a patient, comprising administering to a patient an effective amount of a methylol transfer agent in conjunction with CPB surgery of said patient, wherein said agent is administered to said patient so as to prevent or reduce elevation of IL-6 levels in said patient.

9. The method of claim 8 wherein said agent is selected from the group consisting of taurolidine, taurultam and mixtures thereof.

10. A method of reducing postoperative complications of cardiopulmonary bypass (CPB) surgery in a patient, comprising administering to a patient an effective amount of a methylol transfer agent in conjunction with CPB surgery of said patient, wherein said agent is administered to said patient so as to increase elevation or prevent reduction of IL-10 levels in said patient.

11. The method of claim 10 wherein said agent is selected from the group consisting of taurolidine, taurultam and mixtures thereof.

12. A method of reducing postoperative complications of cardiopulmonary bypass (CPB) surgery in a patient, comprising administering to a patient an effective amount of a methylol transfer agent in conjunction with CPB surgery of said patient, wherein said agent is administered to said patient so as to reduce or prevent systemic endotoxemia in said patient.

13. The method of claim 12 wherein said agent is selected from the group consisting of taurolidine, taurultam and mixtures thereof.

14. A method of reducing postoperative complications of cardiopulmonary bypass (CPB) surgery in a patient, comprising administering to a patient an effective amount of a methylol transfer agent in conjunction with CPB surgery of said patient, wherein said agent comprises a 2% taurolidine solution, wherein said taurolidine solution is administered to said patient at a dose of 250 mL, wherein said patient is administered said dose during said surgery.

15. A method of reducing postoperative complications of cardiopulmonary bypass (CPB) surgery in a patient, comprising administering to a patient an effective amount of a methylol transfer agent in conjunction with CPB surgery of said patient, wherein said patient is administered crystalloid cardioplegia.

16. A method of reducing postoperative complications including arrhythmia associated with cardiopulmonary bypass (CPB) surgery in a patient, comprising administering to a patient an effective amount of a methylol transfer agent in conjunction with CPB surgery of said patient.

17. The method of claim 16 wherein said agent is selected from the group consisting taurolidine, taurultam and mixtures thereof.

18. The method of claim 17 wherein said arrhythmia is sinus-arrhythmia.

19. A method of reducing postoperative complications including ventricular fibrillation associated with cardiopulmonary bypass (CPB) surgery in a patient, comprising administering to a patient an effective amount of a methylol transfer agent in conjunction with CPB surgery of said patient.

20. The method of claim 19 wherein said agent is selected from the group consisting of taurolidine, taurultam and mixtures thereof.

21. A method of reducing postoperative complications including heart fluttering associated with cardiopulmonary bypass (CPB) surgery in a patient, comprising administering to a patient an effective amount of a methylol transfer agent in conjunction with CPB surgery of said patient.

22. The method of claim 21 wherein said agent is selected from the group consisting of taurolidine, taurultam and mixtures thereof.

23. A method of reducing postoperative complications including cytokine activation associated with cardiopulmonary bypass (CPB) surgery in a patient, comprising administering to a patient an effective amount of a methylol transfer agent in conjunction with CPB surgery of said patient.

24. The method of claim 23 wherein said cytokine activation is ameliorated in a perioperative period.

25. The method of claim 24 wherein said agent is selected from the group consisting of taurolidine, taurultam and mixtures thereof.

26. A method of reducing postoperative complications including respiratory compromise associated with cardiopulmonary bypass (CPB) surgery in a patient, comprising administering to a patient an effective amount of a methylol transfer agent in conjunction with CPB surgery of said patient.

27. The method of claim 26, wherein said agent is selected from the group consisting of taurolidine, taurultam and mixtures thereof.

28. A method of reducing postoperative complications including ischemic reperfusion injury associated with cardiopulmonary bypass (CPB) surgery in a patient, comprising administering to a patient an effective amount of a methylol transfer agent in conjunction with CPB surgery of said patient.

29. The method of claim 28 wherein said agent is selected from the group consisting of taurolidine, taurultam and mixtures thereof.

* * * * *